US011063449B2

(12) United States Patent
Cho et al.

(10) Patent No.: US 11,063,449 B2
(45) Date of Patent: Jul. 13, 2021

(54) BATTERY MANAGING METHOD AND APPARATUS TO CONNECT BATTERIES TO ELECTRONIC DEVICES BASED ON STATES OF CHARGE OF THE BATTERIES

(71) Applicant: Samsung Electronics Co., Ltd., Suwon-si (KR)

(72) Inventors: Joon-Kee Cho, Yongin-si (KR); Jongwon Lee, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 686 days.

(21) Appl. No.: 15/883,247

(22) Filed: Jan. 30, 2018

(65) Prior Publication Data

US 2019/0097437 A1 Mar. 28, 2019

(30) Foreign Application Priority Data

Sep. 26, 2017 (KR) .......................... 10-2017-0123989

(51) Int. Cl.
*H02J 7/00* (2006.01)
*A61F 5/01* (2006.01)
*A61H 1/02* (2006.01)

(52) U.S. Cl.
CPC .......... *H02J 7/0024* (2013.01); *A61F 5/0102* (2013.01); *A61H 1/024* (2013.01); *A61H 1/0244* (2013.01); *A61H 1/0262* (2013.01); *A61H 1/0266* (2013.01); *H02J 7/0013* (2013.01); *H02J 7/0022* (2013.01); *H02J 7/0047* (2013.01); *H02J 7/0063* (2013.01); *A61H 2201/0192* (2013.01); *A61H 2201/1207* (2013.01); *A61H 2201/165* (2013.01); *H02J 7/0048* (2020.01)

(58) Field of Classification Search
CPC ........ H02J 7/0054; H02J 7/342; H02J 7/0024; H02J 7/0025; H02J 2007/0067
See application file for complete search history.

(56) References Cited

U.S. PATENT DOCUMENTS

| 6,791,295 | B1 | 9/2004 | Berels |
|---|---|---|---|
| 9,002,413 | B2 | 4/2015 | Furtney |
| 2012/0268070 | A1* | 10/2012 | Park ...................... H02J 7/0024 |
| | | | 320/126 |
| 2013/0102934 | A1 | 4/2013 | Ikeuchi |
| 2016/0241048 | A1 | 8/2016 | Badam et al. |
| 2017/0117733 | A1* | 4/2017 | Pletsch .................... H02J 1/10 |

FOREIGN PATENT DOCUMENTS

| KR | 10-2013-0100523 | 9/2013 |
|---|---|---|
| KR | 10-2016-0014280 | 2/2016 |
| KR | 10-1602877 B1 | 3/2016 |
| KR | 10-2017-0021055 | 2/2017 |
| KR | 20180045655 | 5/2018 |

* cited by examiner

*Primary Examiner* — David V Henze-Gongola
(74) *Attorney, Agent, or Firm* — Harness, Dickey & Pierce, P.L.C.

(57) ABSTRACT

A plurality of electronic devices including batteries and being connected to each other may respectively include battery managing apparatuses that may enable the electronic devices to share power of the batteries included in the electronic devices, more particularly, battery managing apparatuses that may change a mode or a manner to connect the batteries to the electronic devices by comparing states of charge (SoCs) of the batteries.

19 Claims, 8 Drawing Sheets

BATTERY MANAGING METHOD AND APPARATUS TO CONNECT BATTERIES TO ELECTRONIC DEVICES BASED ON STATES OF CHARGE OF THE BATTERIES

CROSS-REFERENCE TO RELATED APPLICATION

This application claims under 35 U.S.C. § 119 to Korean Patent Application No. 10-2017-0123989, filed on Sep. 26, 2017, in the Korean Intellectual Property Office, the entire contents of which are incorporated herein by reference in their entirety.

BACKGROUND

1. Field

At least one example embodiment relates to a method and apparatus to manage batteries included in electronic devices.

2. Description of the Related Art

With the onset of rapidly aging societies, an increasing number of people may experience inconvenience and/or pain from joint problems. Thus, there may be a growing interest in walking assistance apparatuses enabling the elderly and/or patients having joint problems to walk with less effort. When walking assistance apparatuses to be attached to different parts are coupled to each other, batteries included in the walking assistance apparatuses may be used separately.

SUMMARY

Some example embodiments relate to a method of managing batteries included in electronic devices.

In some example embodiment, the method may include obtaining information related to the batteries; comparing residual capacities of the batteries based on the information; and determining a power reception mode for the electronic devices based on the residual capacities, the power reception mode being a scheme for the electronic devices to receive power from different ones of the batteries.

In some example embodiments, the information related to the batteries includes any one or more of amounts of charges remaining in the batteries, maximum amounts of currents outputable from the batteries, and current consumptions of the electronic devices.

In some example embodiments, the comparing the residual capacities includes comparing a maximum value of differences between the residual capacities to a threshold.

In some example embodiments, the determining the power reception mode includes determining the power reception mode as a parallel mode, if the maximum value is less than or equal to the threshold, the parallel mode being a scheme in which the electronic devices receive operating power from each of the batteries in parallel.

In some example embodiments, the comparing the residual capacities includes comparing a sum of current consumptions of the electronic devices to a maximum amount of current outputable from a battery having a greatest residual capacity among the batteries, if the maximum value exceeds the threshold.

In some example embodiments, the determining the power reception mode includes determining the power reception mode as a single mode, if the sum of the current consumptions is less than the maximum amount of current outputable from the battery having the greatest residual capacity, the single mode being a scheme in which the electronic devices receive operating power from the battery having the greatest residual capacity.

In some example embodiments, the determining the power reception mode includes determining the power reception mode as an individual mode, if the sum of the current consumptions is greater than or equal to the maximum amount of current outputable from the battery having the greatest residual capacity, the individual mode being a scheme in which each the electronic devices receive operating power from a local battery of the batteries, the local battery being included in respective ones of the electronic devices.

Some example embodiments relate to a battery managing apparatus included in an electronic device.

In some example embodiments, the battery managing apparatus includes a switch connected to a local battery included in the electronic device; and a power controller configured to, obtain information related to the local battery included in the electronic device and one or more external batteries included in one or more other electronic devices, compare residual capacities of the local battery included in the electronic device and the one or more external batteries included in the one or more other electronic devices based on the information, and determine a power reception mode based on the residual capacities, the power reception mode being a scheme in which the electronic device receives power from one of the local battery and the one or more external batteries.

In some example embodiments, the power controller is configured to compare a maximum value of differences between the residual capacities of the local battery and the one or more external batteries to a threshold.

In some example embodiments, the power controller is configured to determine the power reception mode as a parallel mode, if the maximum value is less than or equal to the threshold, the parallel mode being a scheme in which the electronic device receives operating power from a circuit generated by connecting the local battery and the one or more external batteries in parallel.

In some example embodiments, the power controller is configured to compare a sum of current consumptions of the electronic device and the one or more other electronic devices to a maximum amount of current outputable from a strongest battery, if the maximum value exceeds the threshold, the strongest battery being a battery having a greatest residual capacity among the local battery and the one or more external batteries.

In some example embodiments, the power controller is configured to determine the power reception mode as a single mode, when the sum of the current consumptions is less than the maximum amount of current outputable from the strongest battery, the single mode being a scheme in which the electronic device receives operating power from the strongest battery.

In some example embodiments, the power controller is configured to determine the power reception mode to be an individual mode, if the sum of the current consumptions is greater than or equal to the maximum amount of current outputable from the strongest battery, the individual mode being a scheme in which the electronic device receives operating power from the local battery.

Some example embodiments relate to a battery managing method.

In some example embodiments, the battery managing method includes measuring residual capacities of batteries respectively included in electronic devices; analyzing differences between the residual capacities of the batteries; and determining a power reception mode based on the residual capacities, the power reception mode being a scheme for the electronic devices to receive power from different ones of the batteries.

In some example embodiments, the analyzing includes: determining that the residual capacities are similar to each other when a maximum value of the differences between the residual capacities is less than a threshold.

In some example embodiments, the determining the power reception mode includes determining the power reception mode as one of a parallel mode, a single mode and an individual mode, wherein the parallel mode is a scheme in which the electronic devices receive operating power from a circuit generated by connecting the batteries in parallel, the single mode is a scheme in which the electronic devices receive operating power from one of the batteries, and the individual mode is a scheme in which each of the electronic devices receive operating power from a local battery of the batteries, the local battery being included in respective ones of the electronic devices.

In some example embodiments, the determining of the power reception mode includes determining the power reception mode as the parallel mode, if a maximum value of the differences between the residual capacities is less than or equal to a threshold.

In some example embodiments, the determining of the power reception mode includes determining the power reception mode as the individual mode, if a maximum value of the differences between the residual capacities exceeds a threshold and a sum of current consumptions of the electronic devices is greater than or equal to a maximum amount of current outputable from a strongest battery, the strongest battery being a battery having a greatest residual capacity among the batteries.

In some example embodiments, the determining of the power reception mode includes determining the power reception mode as the single mode, if a maximum value of the differences between the residual capacities exceeds a threshold and a sum of current consumptions of the electronic devices is greater than or equal to a maximum amount of current outputable from a strongest battery, the strongest battery being a battery having a greatest residual capacity among the batteries.

In some example embodiments, the determining of the power reception mode as the single mode includes selecting the strongest battery as a battery to provide the operating power for all the electronic devices.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Specific structural or functional descriptions are provided in the present disclosure to describe examples. The examples may be modified and implemented in various forms, and the scope of the examples is not limited to the descriptions provided in the present specification.

Terms such as first, second, A, B, (a), (b), and the like may be used herein to describe components. Each of these terminologies is not used to define an essence, order or sequence of a corresponding component but used merely to distinguish the corresponding component from other component(s). For example, a first component may be referred to as a second component, and similarly the second component may also be referred to as the first component.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

The terminology used herein is for the purpose of describing particular examples only and is not to be limiting of the examples. As used herein, the singular forms "a", "an", and "the" are intended to include the plural forms as well, unless the context clearly indicates otherwise. It will be further understood that the terms "include/comprise" and/or "have" when used in this specification, specify the presence of stated features, integers, steps, operations, elements, components, and/or combinations thereof, but do not preclude the presence or addition of one or more other features, numbers, steps, operations, elements, components, and/or groups thereof.

Unless otherwise defined, all terms including technical and scientific terms used herein have the same meaning as commonly understood by one of ordinary skill in the art to which examples belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

FIG. 1 illustrates structures of electronic devices including battery managing apparatuses according to at least one example embodiment.

Figure 1:
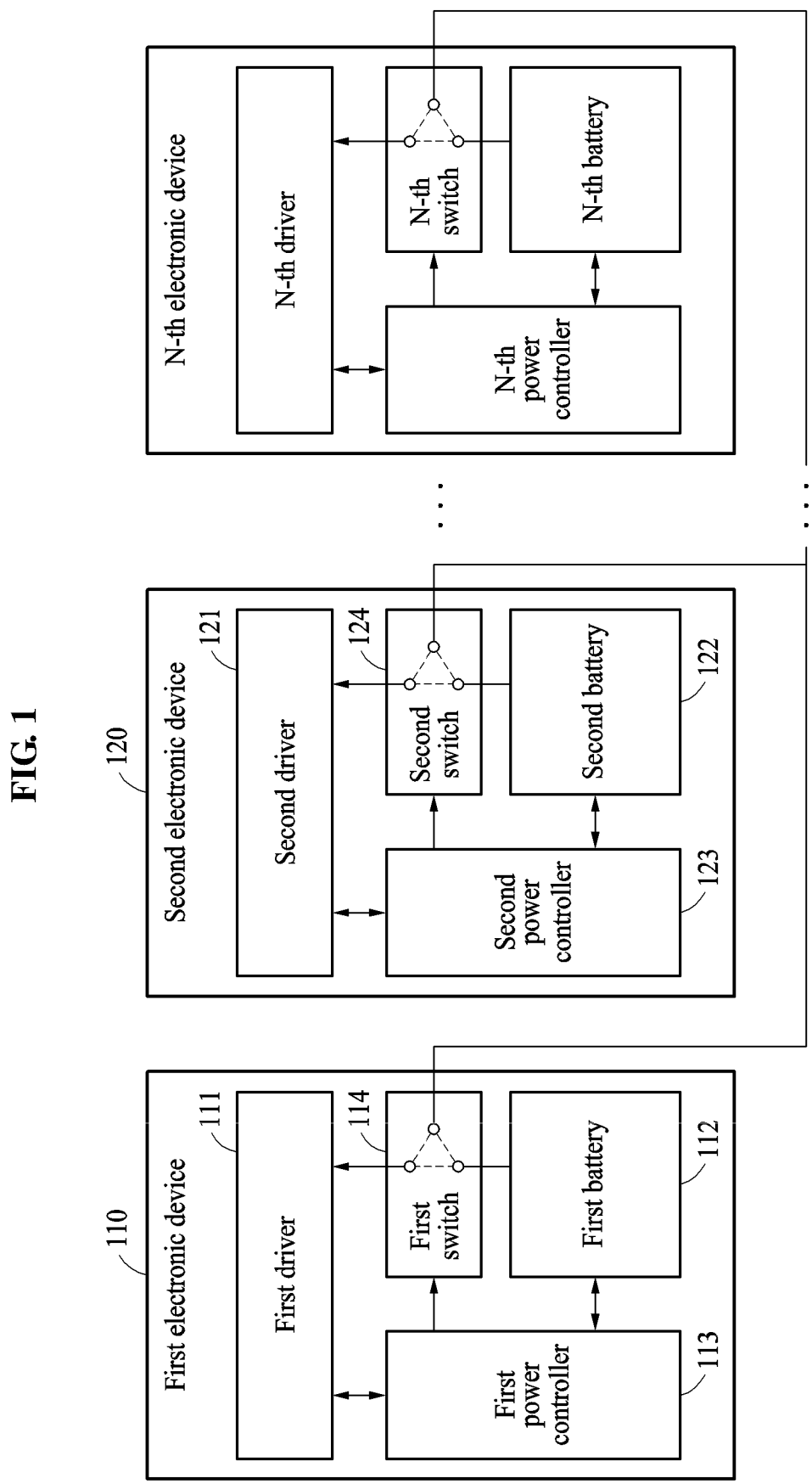
FIG. 1 illustrates structures of electronic devices including battery managing apparatuses according to at least one example embodiment.

Referring to FIG. 1, a system may include N electronic devices including a first electronic device 110, a second electronic device 120, . . . , and an N-th electronic device are illustrated.

Each of the N electronic devices may be a device configured to perform a function corresponding to a design intent using power, and may include a battery that supplies the power.

A battery managing apparatuses may efficiently supply power to the electronic devices 110 and 120. Hereinafter, for ease of description, a battery included in a k-th electronic device will be referred to as a k-th battery. For example, the first electronic device 110 may include a first battery 112, and the second electronic device 120 may include a second battery 122.

Each of the N electronic devices may include a driver configured to perform the functions using the power provided from the battery. For example, the first electronic device 110 may further include a first driver 111, and the second electronic device 120 may further include a second driver 121. Each of the drivers may include any one or any combination of electrical elements to be used to perform the function, for example, an electronic circuit, a motor, a display, a touch screen, a light emitting diode (LED), a speaker, a microphone, a sensor, and a communication module. Hereinafter, for ease of description, a driver included in the k-th electronic device will be referred to as a k-th driver.

Referring to FIG. 1, the N electronic devices may be connected to each other in a wireless or wired manner to share power charged in N batteries respectively included in the N electronic devices. The N electronic devices may be connected using a Bluetooth network, a near field communication (NFC) network, a wireless-fidelity (WiFi) network, an Ethernet for control automation technology (EtherCAT), or a controller area network (CAN). Further, the N electronic devices may be connected to each other in a wireless or wired manner to cooperatively perform a single function. For example, the N electronic devices may be apparatuses to be attached to different body parts of a user to assist motions of the user, for example, walking assistance apparatuses. In another example, the N electronic devices may be electronic devices utilizing the Internet of Things (IoT), the electronic devices to be disposed at different locations and configured to cooperatively operate while sharing information collected at the different locations. In still another example, the N electronic devices may be modular robots configured to operate separately and cooperatively perform a function instructed by an administrator.

The battery managing apparatuses may be respectively included in the N electronic devices being connected to each other, and control connections between batteries and drivers of the N electronic devices. In detail, the battery managing apparatuses may generate a circuit to supply power to the drivers included in the N electronic devices by combining the batteries included in the N electronic devices.

A battery managing apparatus may be associated with each of the N electronic devices.

The battery managing apparatuses may each include a switch, a battery, a communicator and a power controller.

For example, a battery managing apparatus included in the first electronic device 110 may include a first switch 114 configured to connect the first driver 111 and the first battery 112 of the first electronic device 110. The battery managing apparatus included in the first electronic device 110 may further include a first power controller 113 configured to control the first switch 114. Further, a battery managing apparatus included in the second electronic device 120 may include a second switch 124 configured to connect the second driver 121 and the second battery 122. The battery managing apparatus included in the second electronic device 120 may further include a second power controller 123 configured to control the second switch 124.

Hereinafter, for ease of description, a switch included in the k-th electronic device will be referred to as a k-th switch, and a power controller included in the k-th electronic device will be referred to as a k-th power controller.

Each of the switches may include various types of solid state switches a transistor, a metal-oxide-semiconductor field-effect transistor (MOSFET), and/or an electromagnetic relay. However, example embodiments are not limited thereto. The switches may be configured to connect the driver and the battery of the corresponding electronic device to generate the circuit to supply power to the drivers included in the electronic devices.

Each of the batteries may be various types of disposable and/or rechargeable batteries. Disposable batteries may include alkaline, Lithium, Carbon Zinc, and Nickel Oxyhydroxide batteries. Rechargeable batteries may include lead-acid, nickel-cadmium (NiCd), nickel-metal hydride (NiMH), lithium-ion (Li-ion), and lithium-ion polymer (Li-ion polymer) batteries. However, example embodiments are not limited thereto.

The communicators (not shown) may each include one or more transmitters and/or receivers that include hardware and any necessary software to communicate with other electronic devices.

Each of the power controllers may include a memory and processing circuitry (not shown), and The memory (not shown) may include at least one of a volatile memory, non-volatile memory, random access memory (RAM), a flash memory, a hard disk drive, and an optical disk drive.

The processing circuitry may be, but not limited to, a processor, Central Processing Unit (CPU), a controller, an arithmetic logic unit (ALU), a digital signal processor, a microcomputer, a field programmable gate array (FPGA), an Application Specific Integrated Circuit (ASIC), a System-on-Chip (SoC), a programmable logic unit, a microprocessor, or any other device capable of performing operations in a defined manner.

The processing circuitry may be configured, through a layout design or execution of computer readable instructions stored in the memory (not shown), as a special purpose computer distribute the power stored in the batteries to the electronic devices based on information related to the batteries of the electronic devices. Therefore, the processing circuitry may improve the functioning of the electronic devices themselves by efficiently using the power stored in the batteries included in the electronic devices connected to each other.

To distribute the power stored in the batteries to the electronic devices, the k-th switch included in the k-th electronic device may be connected to the k-th driver and the k-th battery, and also to switches included in other electronic devices, more particularly, to batteries included in the other electronic devices. Referring to FIG. 1, the first switch 114 through the N-th switch may be connected to each other to transmit and receive power. Thus, the first electronic device 110 may receive the power of the first battery 112 and the power of at least one of the second battery 122 through the N-th battery through the first switch 114.

A battery managing apparatus may determine whether to receive power to operate an electronic device, that is, power to be supplied to a driver of the electronic device, from a battery included in the electronic device or one or more batteries included in one or more other electronic devices connected to the electronic device. In detail, the battery managing apparatus may select at least one of the batteries included in the electronic devices as a battery to be connected to the driver. The battery managing apparatus may control a switch based on a result of the selection. That is, the battery managing apparatus may connect the selected at least one battery to the driver. For example, the first power controller 113 may select a battery to be connected to the first driver 111 from the first battery 112 through the N-th battery. The first power controller 113 may control the first switch 114 based on a result of selecting the battery to be connected to the first driver 111.

Operations of the first power controller 113 through the N-th power controller selecting batteries to be connected to the corresponding drivers may be performed separately for each power controller, or be performed cooperatively. For example, the operation of the first power controller 113 selecting a battery to be connected to the first driver 111 and the operation of the second power controller 123 selecting a battery to be connected to the second driver 121 may be performed separately. In another example, one of the first power controller 113 through the N-th power controller may select a battery to be connected to the corresponding driver, and broadcast a result of the selection to the remaining power controllers. The first power controller 113 through the N-th power controller may control the corresponding switches based on the broadcast result of the selection. The first power controller 113 through the N-th power controller may determine a power controller to select the battery to be connected to the driver, among the first power controller 113 through the N-th power controller, based on a resource state, for example, a computing speed of a processor included in the driver or a capacity of a memory.

The power controller may control the switch based on one of a plurality of modes to connect the batteries to the drivers. That is, a circuit to supply power to the drivers of the electronic devices may be determined based on the mode selected by the power controller from the plurality of modes. The modes to connect the batteries to the drivers may include a single mode, an individual mode, and a parallel mode.

The single mode may be a mode to connect the batteries to the drivers such that power to operate all the electronic devices is received from one of the batteries included in the electronic devices. Referring to FIG. 1, in the single mode, the first power controller 113 through the N-th power controller may control the first switch 114 through the N-th switch to connect only the first battery 112 to each of the first driver 111 through the N-th driver. In this example, the second battery 122 through N-th battery may not be discharged, and the first battery 112 may supply power to each of the first driver 111 through the N-th driver. The operation of the battery managing apparatuses controlling the switches based on the single mode among the plurality of modes will be described further with reference to FIG. 3.

The individual mode may be a mode to connect the batteries to the drivers such that power to be used by each of the electronic devices is obtained from a battery included in each of the electronic devices. That is, the electronic devices may independently use the corresponding batteries of the electronic devices as if the electronic devices are not connected to each other. Referring to FIG. 1, in the individual mode, the first power controller 113 through the N-th power controller may control the first switch 114 through the N-th switch to connect the k-th battery to the k-th driver. For example, the first power controller 113 may connect the first battery 112 and the first driver 111, and disconnect the second battery 122 through the N-th battery from the first driver 111. The operation of the battery managing apparatuses controlling the switches based on the individual mode among the plurality of modes will be described further with reference to FIG. 4.

The parallel mode may be a mode to connect the batteries to the drivers such that power to operate all the electronic devices is received from a circuit generated by connecting the batteries included in the electronic devices in parallel. Referring to FIG. 1, in the parallel mode, the first power controller 113 through the N-th power controller may control the first switch 114 through the N-th switch to connect the first battery 112 through the N-th battery in parallel. The first power controller 113 through the N-th power controller may connect the first driver 111 through the N-th driver to the circuit generated by connecting the first battery 112 through the N-th battery in parallel through the first switch 114 through the N-th switch. In the parallel mode, charges stored in the first battery 112 through the N-th battery may be discharged equally. The operation of the battery managing apparatuses controlling the switches based on the parallel mode among the plurality of modes will be described further with reference to FIG. 5.

Figure 2:
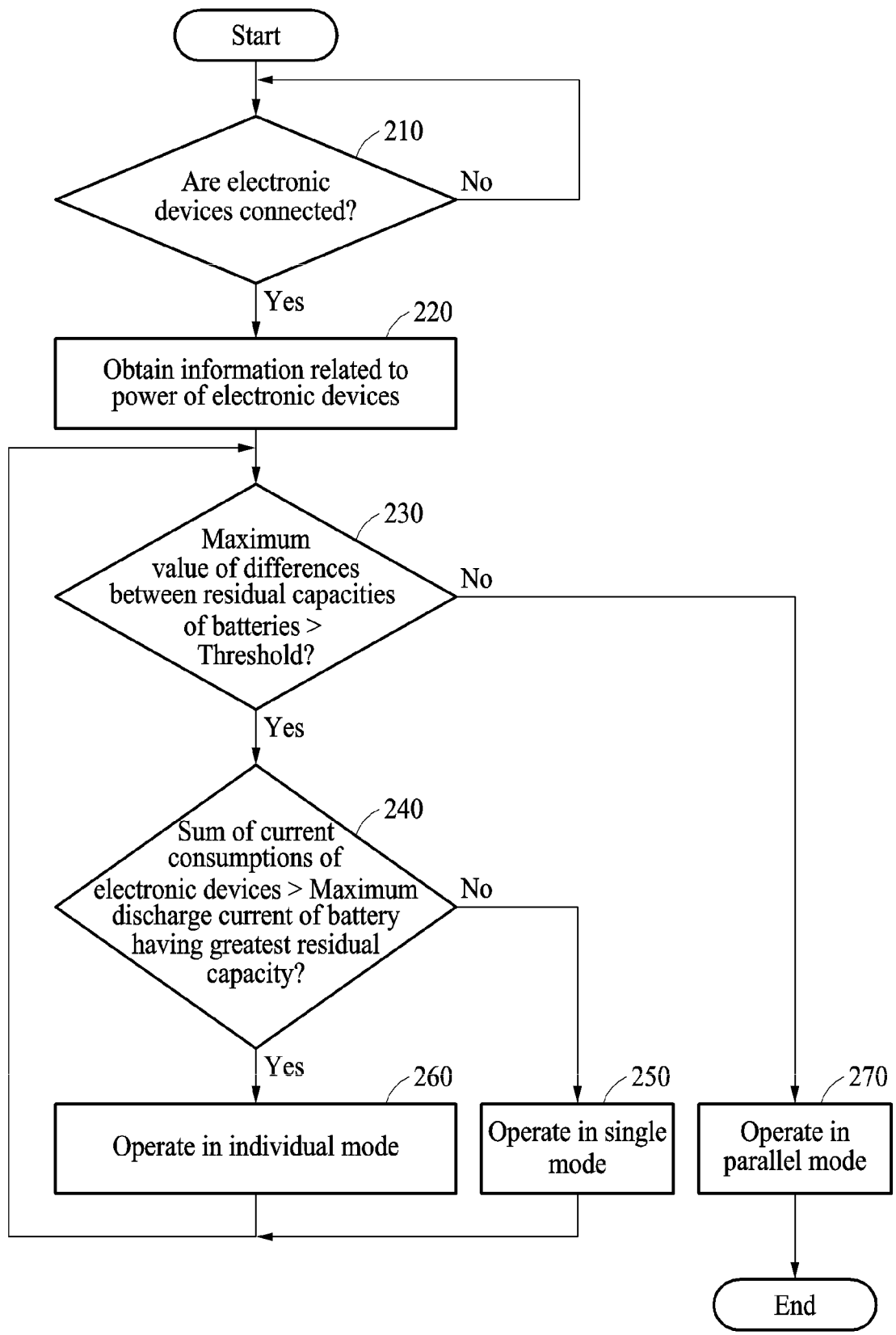
FIG. 2 is a flowchart illustrating an operation performed by battery managing apparatuses according to at least one example embodiment.

FIG. 2 is a flowchart illustrating an operation performed by battery managing apparatuses according to at least one example embodiment. Hereinafter, an operation of battery managing apparatuses generating a circuit to supply power from batteries connected to electronic devices will be described in detail with reference to FIG. 2. The operation of FIG. 2 may be performed by power controllers of battery managing apparatuses respectively included in the electronic devices.

Referring to FIG. 2, in operation 210, the battery managing apparatuses may verify whether a plurality of electronic devices are connected. That is, the battery managing apparatuses may verify whether an electronic device including the battery managing apparatus is connected to another electronic device. In response to verification that the electronic device is connected to the other electronic device, the battery managing apparatuses may verify whether the plurality of connected electronic devices is able to share power to be used to operate drivers based on a connection state.

In operation 220, in response to verification that the plurality of electronic devices are connected, the battery managing apparatuses may obtain information related to power of the electronic devices being connected to each other. The information related to the power of the electronic devices may be shared between the electronic devices that are connected to each other. The information related to the power may include information related to a state of charge (SoC) of a battery, for example, a maximum amount of charge to be stored in the battery, an amount of charge presently stored in the battery, or a voltage of the battery, and information related to a power consumption of an electronic device or a driver of the electronic device, for example, a current power consumption of the electronic device, or a current voltage consumption of the electronic device. The battery managing apparatuses may provide a user with the obtained information through an audio signal or an interface output through a display.

The battery managing apparatuses may identify SoCs of batteries included in the electronic devices from the obtained information. In detail, the battery managing apparatuses may measure residual capacities of the batteries of the electronic devices. The residual capacities of the batteries may be determined based on ratios of amounts of charges presently stored in the batteries to maximum amounts of charges to be stored in the batteries. The battery managing apparatuses may measure the residual capacities of the batteries as percentages.

In operation 230, the battery managing apparatuses may compare differences between the residual capacities of the batteries to a desired (or, alternatively, a preset) threshold. For example, the battery managing apparatuses may compare a maximum value of the differences between the residual capacities of the batteries to the threshold. In another example, the battery managing apparatuses may compare a sum of the differences of the residual capacities of the batteries to the threshold. That is, the battery managing apparatuses may compare the residual capacities of the batteries to verify whether the residual capacities of the batteries are similar to each other.

In a case in which the differences between the residual capacities of the batteries are greater than or equal to the threshold, for example, in a case in which the maximum value of the differences between the residual capacities of the batteries is greater than or equal to the threshold or in a case in which the sum of the differences between the residual capacities of the batteries is greater than or equal to the threshold, the battery managing apparatus may proceed to operation 240 to determine whether to operate in the individual mode or the single mode.

In operation 240, the battery managing apparatuses may compare a sum of current consumptions of the electronic devices to a maximum amount of current to be output from a battery having a greatest residual capacity among the batteries, that is, a maximum discharge current of the battery having the greatest residual capacity. That is, in a case in which the residual capacities of the batteries are not similar to each other, the battery managing apparatuses may compare the power consumptions of the electronic devices to a maximum power to be supplied from the battery having the greatest residual capacity among the batteries.

In a case in which the sum of the current consumptions of the electronic devices is less than the maximum discharge current of the battery having the greatest residual capacity among the batteries, the battery managing in operation 250, the battery managing apparatuses may set a power reception mode in which the electronic devices receive power from the batteries, that is, a mode to connect the batteries to the drivers, to be a single mode. That is, the battery managing apparatuses may supply power to the electronic devices based on the single mode.

As described above, the single mode may be a mode in which one of the batteries included in the electronic devices supplies power to all the electronic devices. The battery managing apparatuses may determine the battery having the greatest residual capacitor among the batteries to be a battery to supply power to all the electronic devices. Thus, charges stored in the battery having the greatest residual capacity may be first supplied to the electronic devices. Remaining batteries except for the battery having the greatest residual capacity may not be used in the single mode.

In a case in which the sum of the current consumptions of the electronic devices is greater than or equal to the maximum discharge current of the battery having the greatest residual capacity among the batteries, in operation 260, the battery managing apparatuses may set the power reception mode to be an individual mode. That is, the battery managing apparatuses may supply power to the electronic devices based on the individual mode.

The individual mode may be a mode in which a battery included in each of the electronic devices supplies power to a corresponding electronic device, that is, a mode in which the electronic devices independently use the batteries. In a case in which the differences between the residual capacities of the batteries are greater than or equal to the threshold, the battery managing apparatuses may use the batteries based on one of the individual mode and the single mode to actively handle the power consumptions of the electronic devices.

In summary, in a case in which the differences between the residual capacities of the batteries are greater than or equal to the threshold, and the power consumptions of the electronic devices are less than or equal to a maximum power to be supplied from the battery having the greatest residual capacity among the batteries, the battery managing apparatuses may first connect the battery having the greatest residual capacity to the electronic devices. Thus, although SoCs of the batteries are not balanced in advance, the residual capacities of the batteries may be balanced with each other over time. In a case in which the differences between the residual capacities of the batteries are greater than or equal to the threshold, and the power consumptions of the electronic devices exceed the maximum power to be supplied from the battery having the greatest residual capacity among the batteries, the battery managing apparatuses may enable each of the electronic devices to use the corresponding battery included in each of the electronic devices. Thus, the battery managing apparatuses may reduce a probability of (or, alternatively, prevent) a situation in which the battery having the greatest residual capacity outputs a current exceeding the maximum discharge current, thereby preventing a situation in which a load is concentrated in the battery having the greatest residual capacity.

Alternatively, in a case in which the residual capacities of the batteries are balanced with each other over time, that is, in a case in which, in operation 250, the battery managing apparatus determines that the differences between the residual capacities of the batteries are less than the threshold the battery managing apparatuses may proceed to operation S270.

In operation S270, the battery managing apparatus may determine the power reception mode to be a parallel mode. That is, the battery managing apparatuses may supply power to the electronic devices based on the parallel mode. For example, in a case in which the maximum value of the differences between the residual capacities of the batteries is less than the threshold, or in a case in which the sum of the residual capacities of the batteries is less than the threshold, the battery managing apparatuses may supply power to the electronic devices based on the parallel mode.

The parallel mode may be a mode in which power to operate all the electronic devices is obtained using a circuit generated by connecting the batteries included in the electronic devices in parallel. The battery managing apparatuses may control switches to connect the batteries in parallel. The battery managing apparatuses may connect drivers of the electronic devices to the circuit generated by connecting the batteries in parallel. The power to be used to operate the electronic devices is provided from the circuit generated by connecting the batteries in parallel, and thus equal amounts of charges may be discharged from the batteries. Since the batteries are used equally, a cooperative operation time of the electronic devices may increase.

Hereinafter, an operation of the battery managing apparatuses included in the electronic devices controlling the corresponding switches in the single mode, the individual mode, and the parallel mode will be described further with reference to FIGS. 3 through 5, respectively.

Figure 3:
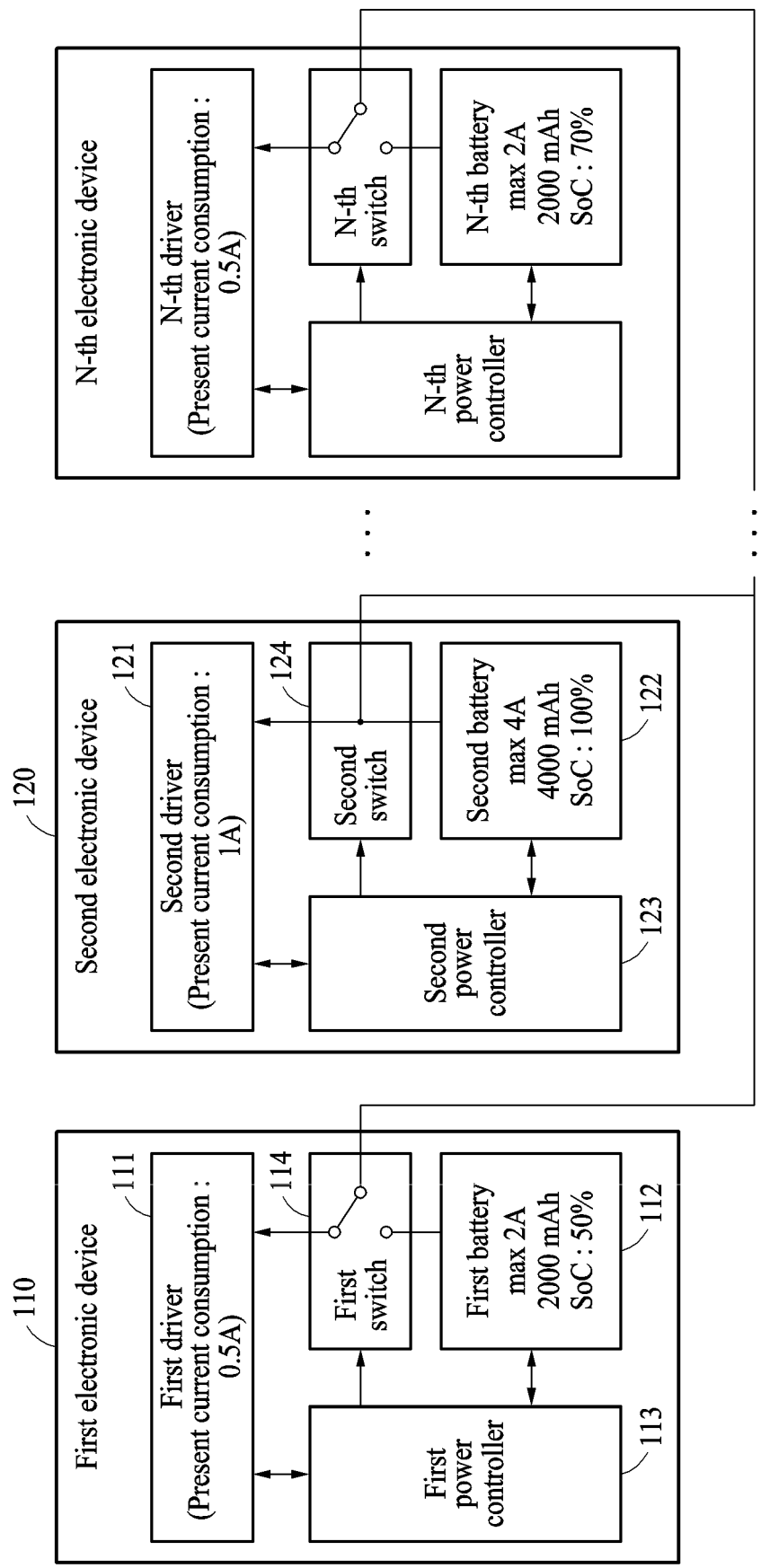
FIG. 3 illustrates an operation of the battery managing apparatuses of FIG. 1 controlling switches in a single mode.

FIG. 3 illustrates an operation of the battery managing apparatuses of FIG. 1 controlling switches in a single mode.

Referring to FIG. 3, it may be assumed that the first battery 112 has an SoC of 50%, a capacity of 2,000 milliamperes hour (mAh), and a maximum discharge current of 2 amperes (A), the second battery 122 has an SoC of 100%, a capacity of 4,000 mAh, and a maximum discharge current of 4 A, and the N-th battery has an SoC of 70%, a capacity of 2,000 mAh, and a maximum discharge current of 2 A. Further, it may also be assumed that the first driver 111 is presently consuming a current of 0.5 A, the second driver 121 is presently consuming a current of 1 A, the N-th driver is presently consuming a current of 0.5 A, and thus a sum of the currents that the first driver 111 through the N-th driver are presently consuming is less than 4 A.

The battery managing apparatuses may compare the SoCs of the batteries to verify whether the SoCs of the batteries are similar to each other. To verify whether the SoCs of the batteries are similar to each other, the battery managing apparatuses may measure differences between the SoCs of the batteries. Referring to FIG. 3, a difference between the SoCs of the first battery 112 and the second battery 122 is 50%, and a difference between the SoCs of the first battery 112 and the N-th battery is 20%, and a difference between the SoCs of the second battery 122 and the N-th battery is 30%. The battery managing apparatuses may measure differences between SoCs of two different batteries, and thus may measure differences of SoCs from $_NC_2$ battery combinations with respect to the N batteries.

The battery managing apparatuses may compare a maximum value of the differences between the SoCs of the two different batteries to a desired (or, alternatively, a preset) threshold, and determine whether to connect the first battery 112 through the N-th battery based on a parallel mode. The threshold may be preset or set empirically. In the example of FIG. 3, it may be assumed that the maximum value of the differences between the SoCs of the two different batteries is 50% which is the difference between the SoCs of the first battery 112 and the second battery 122, and the threshold is 5%. Since the maximum value of the differences between the SoCs of the batteries is greater than the threshold, the battery managing apparatuses may determine to not connect the first battery 112 through the N-th battery based on the parallel mode.

In a case in which it is determined to not connect the first battery 112 through the N-th battery based on the parallel mode, the battery managing apparatuses may compare a sum of the currents that the electronic devices are presently consuming, that is, a sum of the currents that the first driver 111 through the N-th driver are presently consuming, to a maximum discharge current of a battery having a greatest SoC among the first battery 112 through the N-th battery. Based on a result of the comparing, the battery managing apparatuses may select one of a single mode and an individual mode as a mode to connect the first battery 112 through the N-th battery to the first driver 111 through the N-th driver.

In detail, in a case in which the sum of the currents that the first driver 111 through the N-th driver are consuming is less than the maximum discharge current of the battery having the greatest SoC among the first battery 112 through the N-th battery, the battery managing apparatuses may determine the mode to connect the first battery 112 through the N-th battery to the first driver 111 through the N-th driver to be the single mode. Referring to FIG. 3, it may be learned that the second battery 122 having the SoC of 100% is the battery having the greatest SoC among the first battery 112 through the N-th battery. Thus, the battery managing apparatuses may compare the maximum discharge current of 4 A of the second battery 122 to the sum of the currents that the first driver 111 through the N-th driver are presently consuming. Since the sum of the currents that the first driver 111 through the N-th driver are presently consuming is less than 4 A, the battery managing apparatus may determine the mode to connect the first battery 112 through the N-th battery to the first driver 111 through the N-th driver to be the single mode.

As described above, in the single mode, the battery managing apparatuses may determine the battery having the greatest residual capacity among the batteries to be a battery to supply power to all the electronic devices. The information related to the power of the first electronic device 110 through the N-th electronic device, for example, SoCs and maximum discharge currents of the first battery 112 through the N-th battery, and currents that the first driver 111 through the N-th driver are presently consuming, may be shared among the battery managing apparatuses respectively included in the first electronic device 110 through the N-th electronic device. Thus, the battery managing apparatuses may determine the same mode to connect the batteries to the drivers and the same battery to supply power to all the electronic devices. Referring to FIG. 3, the battery managing apparatuses included in the first electronic device 110 through the N-th electronic device may determine to connect the batteries and the drivers based on the single mode, and select the battery 122 having the greatest SoC from the first battery 112 through the N-th battery as the battery to supply power to all the electronic devices.

The battery managing apparatuses may control the corresponding switches based on a result of selecting the mode to connect the batteries to the drivers. Since the second battery 122 is selected as the battery to supply power to all the electronic devices, the second power controller 123 may control the second switch 124 connected to the second battery 122 to connect the second battery 122 to the second driver 121, and output the power of the second battery 122 to an outside. For example, the second power controller 123 may control the second switch 124 to connect the second battery 122 to a common node to which all of the first switch 114 through the N-th switch are connected.

Among the first power controller 113 through the N-th power controller, an x-th power controller except for the second power controller 123 (that is, $1 \leq x \leq N$, $x \neq 2$) may control an x-th switch to disconnect an x-th battery from an x-th driver and connect the x-th driver to the second battery 122. Referring to FIG. 3, the first power controller 113 may control the first switch 114 to disconnect the first battery 112 from the first driver 111, and connect the first driver 111 to the common node to which all of the first switch 114 through the N-th switch are connected. Thus, the power stored in the second battery 122 having the greatest SoC may be used first.

In a case in which the battery having the greatest SoC has changed to another battery over time as the power stored in the battery having the greatest SoC is used first, the battery managing apparatuses may change the battery connected to the first driver 111 through the N-th driver. For example, it may be assumed that the N-th battery having the SoC of 70% is a battery having a second greatest SoC while the second battery 122 has the greatest SoC of 100%. In a case in which the SoC of the second battery 122 is less than 70%, the battery managing apparatuses may connect the N-th battery to the first driver 111 through the N-th driver, instead of the second battery 122. In another example, the battery managing apparatuses may connect the second battery 122 and the N-th battery to the first driver 111 through the N-th driver at a point in time at which the SoC of the second battery 122 matches the SoC of the N-th battery. In this example, the number of batteries connected to the first driver 111 through the N-th driver may gradually increase, and equal amounts of charges of the one or more batteries connected to the first driver 111 through the N-th driver may be discharged. That is, the battery managing apparatuses may increase the number of batteries connected to the first driver 111 through the N-th driver in the single mode as the SoC of the battery having the greatest SoC decreases.

Amounts of the currents that the first driver 111 through the N-th driver are presently consuming may change based on a load or a function performed by the first driver 111 through the N-th driver. When a sum of the currents that the first driver 111 through the N-th driver are presently consuming exceeds a maximum discharge current of the battery having the greatest SoC (in the example of FIG. 3, the maximum discharge current of 4 A of the second battery 122), the battery may output a current greater than or equal to the maximum discharge current, which may cause a malfunction. In the single mode, to prevent the situation, the battery managing apparatuses may determine whether to switch from the single mode to an individual mode by comparing the sum of the currents that the electronic devices are presently consuming to the maximum discharge current of the battery having the greatest SoC.

Figure 4:
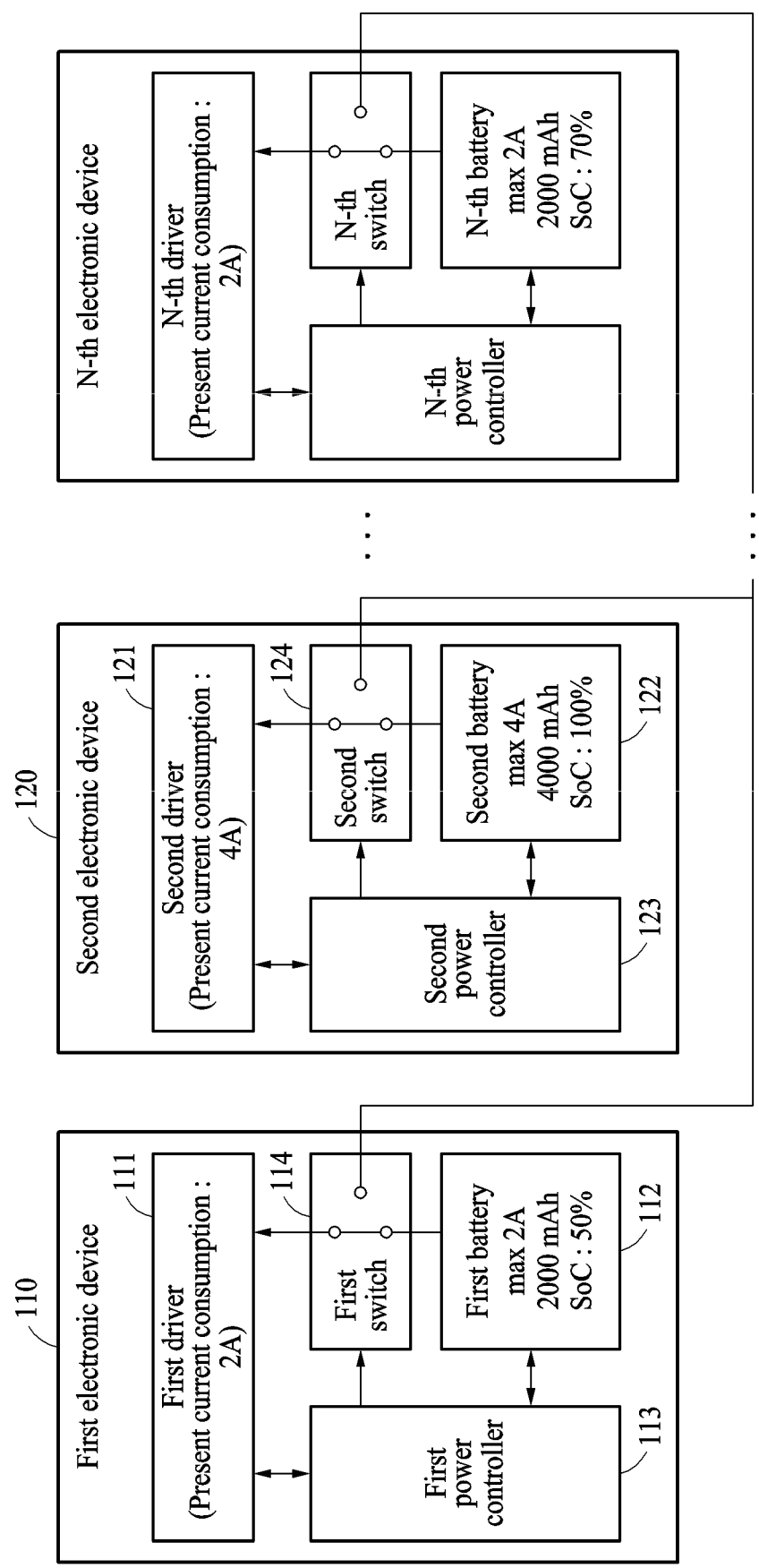
FIG. 4 illustrates an operation of the battery managing apparatuses of FIG. 1 controlling switches in an individual mode.

FIG. 4 illustrates an operation of the battery managing apparatuses of FIG. 1 controlling switches in an individual mode.

Referring to FIG. 4, it may be assumed that the SoCs, the capacities, and the maximum discharge currents of the first battery 112 through the N-th battery are the same as in the example of FIG. 3. However, it may be assumed that the first driver 111 is presently consuming a current of 2 A, the second driver 121 is presently consuming a current of 4 A, the N-th driver is presently consuming a current of 2 A, and thus a sum of the currents that the first driver 111 through the N-th driver are presently consuming is greater than 4 A.

Since the SoCs of the first battery 112 through the N-th battery are the same as in the example of FIG. 3, that is, the SoCs of the batteries are not similar to each other, the battery managing apparatuses may determine to not connect the first battery 112 through the N-th battery based on a parallel mode. In this example, the battery managing apparatuses may compare the sum of the currents that the first driver 111 through the N-th driver are presently consuming to a maximum discharge current of a battery having a greatest SoC among the first battery 112 through the N-th battery. Based on a result of the comparing, the battery managing apparatuses may select one of a single mode and an individual mode as a mode to connect the first battery 112 through the N-th battery to the first driver 111 through the N-th driver.

In detail, in a case in which the sum of the currents that the first driver 111 through the N-th driver are presently consuming is greater than or equal to the maximum discharge current of the battery having the greatest SoC among the first battery 112 through the N-th battery, the battery managing apparatuses may determine the mode to connect the first battery 112 through the N-th battery to the first driver 111 through the N-th driver to be the individual mode. Referring to FIG. 4, the battery managing apparatuses may compare the maximum discharge current of 4 A of the second battery 122 having the greatest SoC to the sum of the currents that the first driver 111 through the N-th driver are presently consuming. Since the sum of the currents that the first driver 111 through the N-th driver are presently consuming is greater than 4 A, the battery managing apparatuses may determine the mode to connect the first battery 112 through the N-th battery to the first driver 111 through the N-th driver to be the individual mode.

In the individual mode, an x-th power controller ($1 \leq x \leq N$) may control an x-th switch to connect an x-th battery to an x-th driver, and disconnect remaining batteries except for the x-th battery from the x-th driver. Referring to FIG. 4, the second power controller 123 may control the second switch 124 to connect the second battery 122 to the second driver 121, and disconnect the second driver 121 from a common node to which all of the first switch 114 through the N-th switch are connected, thereby disconnecting the remaining batteries except for the second battery 122 from the second driver 121.

Thus, the electronic devices may operate as if the electronic devices do not share the batteries. The battery managing apparatuses may monitor the sum of the currents that the first driver 111 through the N-th driver are presently consuming, and change the mode to connect the batteries to the drivers from the individual mode to the single mode. For example, in a case in which the sum of the currents that the first driver 111 through the N-th driver are presently consuming is less than or equal to the maximum discharge current of the battery having the greatest SoC, the battery managing apparatuses may change the mode to connect the batteries to the drivers from the individual mode to the single mode. Since the battery managing apparatuses may switch the mode to connect the batteries to the drivers between the individual mode and the single mode based on the sum of the currents that the first driver 111 through the N-th driver are presently consuming, the battery managing apparatuses may actively handle power consumptions of the electronic devices. Furthermore, the battery managing apparatuses may prevent a malfunction that may occur when the battery output a current greater than or equal to the maximum discharge current.

During a period except for a period during which the sum of the current consumptions of the electronic devices is greater than or equal to the maximum discharge current of the battery having the greatest SoC, the battery managing apparatuses may first use the power of the battery having the greatest SoC in the single mode, and thus SoCs of the batteries may be equal over time. In a case in which the SoCs of the batteries are equal, the battery managing apparatuses may change the mode to connect the batteries to the drivers to a parallel mode.

Figure 5:
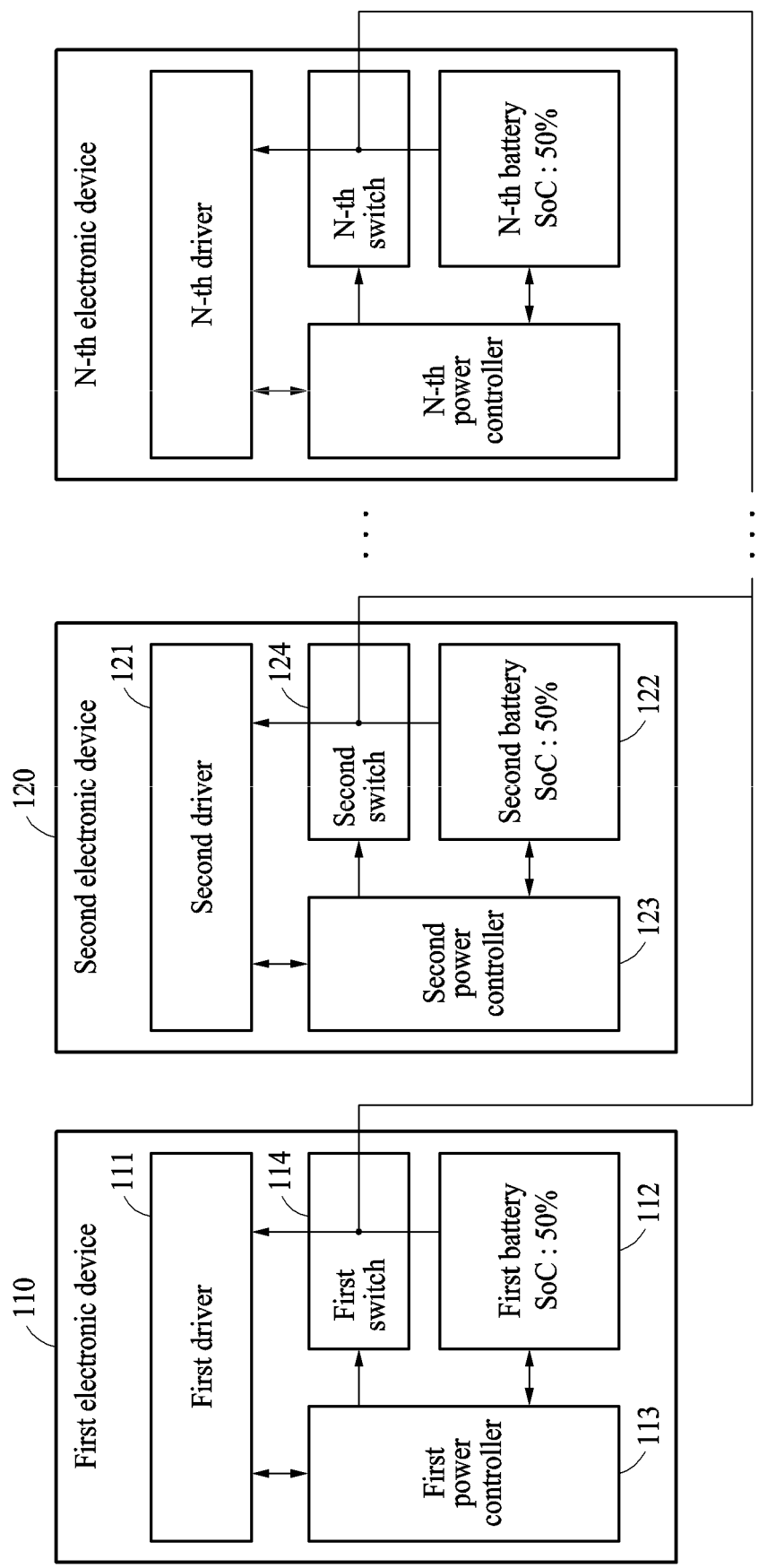
FIG. 5 illustrates an operation of the battery managing apparatuses of FIG. 1 controlling switches in a parallel mode.

FIG. 5 illustrates an operation of the battery managing apparatuses of FIG. 1 controlling switches in a parallel mode.

Referring to FIG. 5, it may be assumed that the first battery 112 through the N-th battery have equal SoCs of 50%. Thus, all differences between the SoCs of the batteries may be 0%. Since a maximum value of differences between SoCs of two different batteries is less than a threshold of 5%, the battery managing apparatuses may determine to connect the first battery 112 through the N-th battery based on a parallel mode.

In the parallel mode, an x-th power controller (1≤x≤N) may control an x-th switch to connect all of the first battery 112 through the N-th battery to an x-th driver. Referring to FIG. 5, the first power controller 113 may control the first switch 114 to connect the first battery 112 to the first driver 111, and connect the first driver 111 to a common node to which all of the first switch 114 through the N-th switch are connected. Similarly, the second power controller 123 through the N-th power controller may control the second switch 124 through the N-th switch. Thus, the first battery 112 through the N-th battery and the first driver 111 through the N-th driver may be connected to the common node to which all of the first switch 114 through the N-th switch are connected.

That is, the first driver 111 through the N-th driver may be supplied with power from a circuit generated by connecting the first battery 112 through the N-th battery in parallel. Since the first battery 112 through the N-th battery are connected in parallel, amounts of charges discharged from the first battery 112 through the N-th battery may be equal. Thus, the first battery 112 through the N-th battery may supply power to the same load.

As described above, the power controllers may compare SoCs of the batteries in a unit of percentage. In another example, the power controllers may determine values obtained by applying residual capacities of the batteries that express the SoCs of the batteries as percentages to maximum amounts of charges to be stored in the batteries, and compare the determined values. For example, in a case of comparing the SoCs of the first battery 112 and the second battery 122 of FIG. 3, the battery managing apparatuses may compare 2,000 mAh×50%=1,000 mAh obtained as the SoC of the first battery 112 by applying the residual capacity of 50% of the first battery 112 expressed as percentage to the maximum amount of charge of 2,000 mAh to 4,000 mAh×100%=4,000 mAh which is the SoC of the second battery 122. Based on a result of comparing the values obtained by applying the residual capacities of the batteries to the maximum amounts of charges to be stored in the batteries, the power controllers may select one of the single mode, the individual mode, and the parallel mode similarly as described with reference to FIGS. 3 through 5.

As described above, the batteries may be connected in parallel when the SoCs of the batteries are equal. Thus, unnecessary discharges or heat emissions of batteries caused when batteries having different SoCs are connected may be prevented. The unnecessary discharges or heat emissions of the batteries may include, for example, discharges or heat emissions caused when a battery having a relatively great SoC charges a battery having a relatively small SoC. When the unnecessary discharges or heat emissions of the batteries are prevented, a time of use of the batteries, that is, a time of use of the electronic devices, may increase.

Furthermore, in a situation in which the electronic devices need to cooperatively perform a single function, suspension of the performance of the function in remaining electronic devices when one of batteries of the electronic devices is discharged may be prevented.

Figure 6:
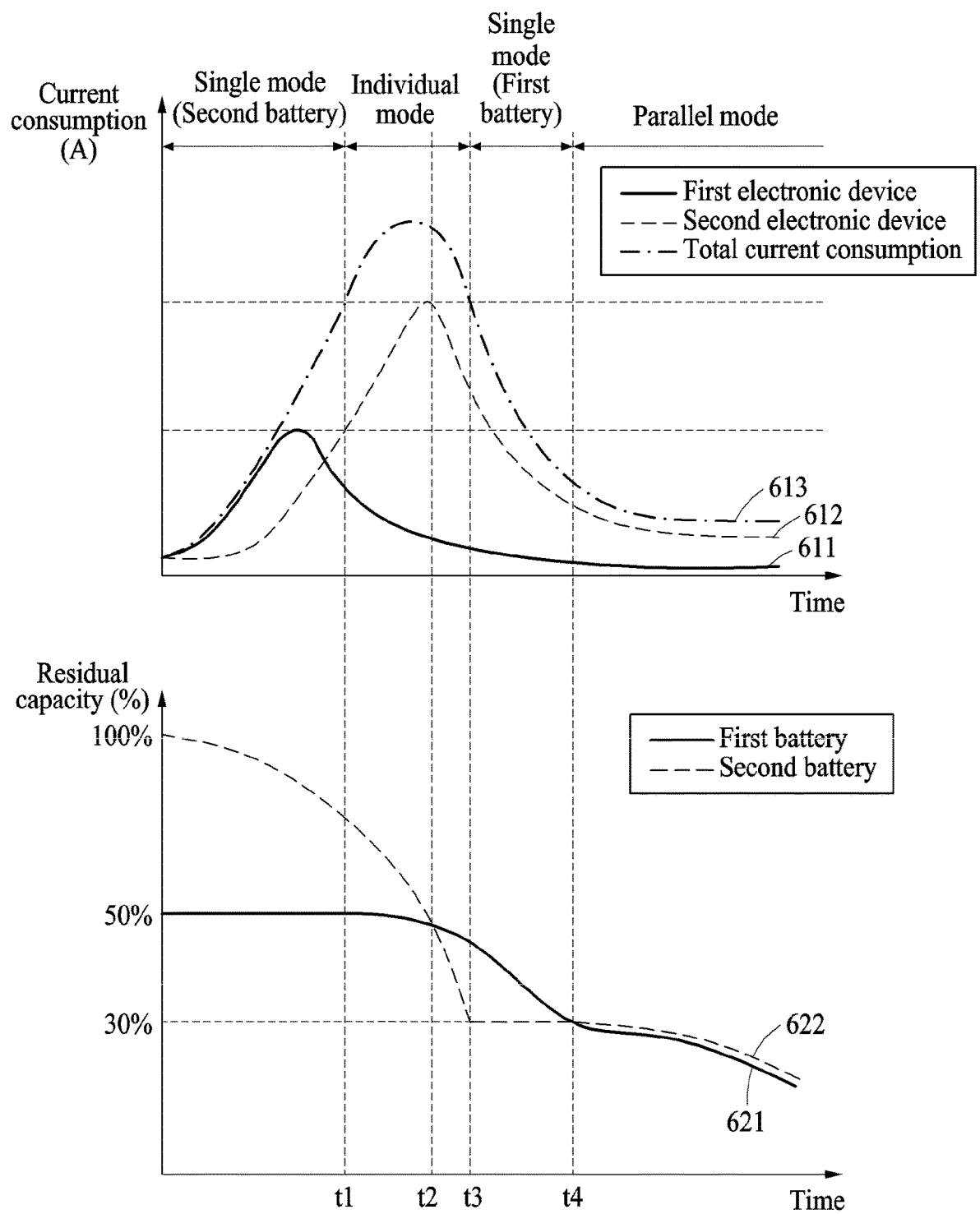
FIG. 6 illustrates current consumptions of electronic devices including battery managing apparatuses and residual capacities of batteries included in the electronic devices with respect to time according to at least one example embodiment.

FIG. 6 illustrates current consumptions of electronic devices including battery managing apparatuses and residual capacities of batteries included in the electronic devices with respect to time according to at least one example embodiment. Hereinafter, it may be assumed that a first electronic device and a second electronic device are connected to each other.

Referring to FIG. 6, a curve 611 may indicate a current consumption of the first electronic device with respect to time, and a curve 612 may indicate a current consumption of the second electronic device with respect to time. Further, a curve 613 may indicate a sum of the current consumptions of the first electronic device and the second electronic device with respect to time.

A battery included in the first electronic device will be referred to as a first battery, and a battery included in the second electronic device will be referred to as a second battery. Hereinafter, it may be assumed that the first battery has a maximum discharge current of 2 A, and the second battery has a maximum discharge current of 4 A. Battery managing apparatuses included in the first electronic device and the second electronic device may manage residual capacities of the first battery and the second battery. Referring to FIG. 6, a curve 621 may indicate the residual capacity of the first battery with respect to time, and a curve 622 may indicate the residual capacity of the second battery with respect to time.

At a point in time t0, the residual capacity of the first battery is 50%, and the residual capacity of the second battery is 100%. Thus, the battery managing apparatuses may measure a difference between the residual capacities of the first battery and the second battery to be 50% at the point in time t0. In a case in which the difference between the residual capacities of the first battery and the second battery is not 0%, that is, the residual capacities of the batteries included in the electronic devices being connected to each other are not equal, the battery managing apparatuses may supply power of the first battery and the second battery to the first electronic device and the second electronic device based on a single mode or an individual mode, rather than a parallel mode. In an example, the battery managing apparatuses may compare the difference between the residual capacities of the batteries included in the electronic devices being connected to each other to a preset threshold. In a case in which the difference between the residual capacities of the batteries is greater than or equal to the preset threshold, the battery managing apparatuses may supply the power of the batteries to the electronic devices based on the single mode or the individual mode, rather than the parallel mode.

Since the difference between the residual capacities of the first battery and the second battery is not 0% at the point in time t0, the battery managing apparatuses may select a mode to supply power of the first battery and the second battery to the first electronic device and the second electronic device between a single mode and an individual mode. The battery managing apparatuses may select one of the single mode and the individual mode based on information related to power consumptions of the first electronic device and the second electronic device and information related to power to be supplied from a battery having a greater residual capacity between the first battery and the second battery. In detail, the battery managing apparatuses may select one of the single mode and the individual mode by comparing a sum of currents that the first electronic device and the second electronic device are presently consuming to a maximum discharge current of the battery having the greater residual capacity between the first battery and the second battery.

In a case in which the sum of the currents that the first electronic device and the second electronic device are presently consuming is less than the maximum discharge current of the battery having the greater residual capacity between the first battery and the second battery, the battery managing apparatuses may supply the power of the batteries to the electronic devices based on the single mode. Furthermore, the battery managing apparatuses may determine the battery having the greater residual capacity between the first battery and the second battery to be a battery to operate all of the first electronic device and the second electronic device. Referring to FIG. 6, the battery having the greater residual capacity at the point in time t0 is the second battery having the residual capacity of 100%. Since the sum of the current consumptions of the first electronic device and the second electronic device is less than the maximum discharge current of 4 A of the second battery at the point in time t0, the battery managing apparatuses may supply the power of the second battery having the greater residual capacity to the first electronic device and the second electronic device based on the single mode. The operation of the battery managing apparatuses controlling switches to supply the power of the second battery having the greater residual capacity to the first electronic device and the second electronic device may be performed similarly as described with reference to FIG. 3.

The battery managing apparatuses may change a mode to connect batteries to electronic devices among the single mode, the individual mode, and the parallel mode by tracking the residual capacities of the batteries and the sum of the current consumptions of the electronic devices. Referring to FIG. 6, it may be assumed that the sum of the currents that the first electronic device and the second electronic device are presently consuming exceeds the maximum discharge current of 4 A of the second battery at a point in time t1. In a case in which the sum of the currents that the first electronic device and the second electronic device are presently consuming exceeds the maximum discharge current of the battery having the greater residual capacity between the first battery and the second battery, the battery managing apparatuses may supply the power of the batteries to the electronic devices based on the individual mode. Thus, the battery managing apparatuses may supply the power of the first battery to the first electronic device and the power of the second battery to the second electronic device from the point in time t1. Since the power of both the first battery and the second battery is used from the point in time t1, the residual capacities of both the first battery and the second battery may be reduced. The operation of the battery managing apparatuses supplying the power of the first battery to the first electronic device and the power of the second battery to the second electronic device in the individual mode may be performed similarly as described with reference to FIG. 4.

In the individual mode, current consumptions of the electronic devices are different, and thus the battery having the greater residual capacity between the batteries may change. Referring to FIG. 6, it may be assumed that the residual capacity of the second battery is greater than the residual capacity of the first battery before a point in time t2, and the residual capacity of the first battery is greater than the residual capacity of the second battery after the point in time t2. Thus, after the point in time t2, the battery managing apparatuses may compare the maximum discharge current of 2 A of the first battery to the sum of the current consumptions of the first electronic device and the second electronic device. At a point in time t3, the sum of the current consumptions of the first electronic device and the second electronic device decreases to be below the maximum discharge current of 2 A of the first battery. Thus, the battery managing apparatuses may supply the power of the first battery to the first electronic device and the second electronic device from the point in time t3 based on the single mode. Thus, after the point in time t3, the residual capacity of the second battery may not change, and only the residual capacity of the first battery may decrease.

In a case in which the residual capacities of the batteries included in the electronic devices being connected to each other are equal, the battery managing apparatuses may supply the power of the first battery and the second battery to the first electronic device and the second electronic device based on the parallel mode. In an example, the battery managing apparatuses may compare a difference between the residual capacities of the batteries included in the electronic devices being connected to each other to a preset threshold. In a case in which the difference between the residual capacities of the batteries is less than the threshold, the battery managing apparatuses may supply the power of the batteries to the electronic devices based on the parallel mode.

Referring to FIG. 6, at a point in time t4, the residual capacity of the first battery and the residual capacity of the second battery may be equally 30%. Thus, the battery managing apparatuses may connect the first battery and the second battery in parallel, and supply power output from a circuit generated by connecting the first battery and the second battery in parallel to the first electronic device and the second electronic device from the point in time t4 based on the parallel mode. The operation of the battery managing apparatuses connecting the first battery and the second battery in parallel, and supplying the power output from the circuit generated by connecting the first battery and the second battery in parallel to the first electronic device and the second electronic device may be performed similarly as described with reference to FIG. 5.

Since the first electronic device and the second electronic device are supplied with the power from the circuit generated by connecting the first battery and the second battery in parallel, the first battery and the second battery may output the same amounts of power in the parallel mode. Referring to FIG. 6, the residual capacities of the first battery and the second battery may decrease at the same speeds after the point in time t4. Since the charge of the second battery having a relatively less residual capacity may not be used up first, a time of simultaneous use of the first electronic device and the second electronic device may increase.

In summary, a plurality of electric devices being connected to each other and including batteries may include respective battery managing apparatuses. The battery managing apparatuses may enable the electronic devices to share power of the batteries included in the electronic devices. In detail, the battery managing apparatuses may change a mode or a manner to connect the batteries to the electronic devices by comparing SoCs of the batteries. The battery managing apparatuses may connect all the electronic devices to a battery charged with a greatest amount of charge among the batteries, thereby discharging the battery charged with the greatest amount of charge first. In a case in which the electronic devices use currents greater than a maximum current to be output from the battery discharged first, the battery managing apparatuses may connect the electronic devices to the corresponding batteries included in the electronic devices. When the SoCs of the batteries are balanced as the battery charged with the greatest amount of charge is discharged first, the battery managing apparatuses may supply the same amounts of currents output from the batteries to the electronic devices using a circuit generated by connecting the batteries in parallel.

In an example, a battery managing apparatus may be included in a walking assistance apparatus configured to assist a walking motion of a user. Walking assistance apparatuses to which battery managing apparatuses are applied may be attached to different body parts of the user to cooperatively perform the function to assist the walking motion of the user. The battery managing apparatus may be mounted on the walking assistance apparatus in a form of a separate board, for example, a printed circuit board (PCB), to be disconnected from a battery and connected to a terminal of the battery. In another example, the battery managing apparatus may be implemented in a form of a pack in which a board and a battery is integrated, and mounted on the walking assistance apparatus.

Figure 7:
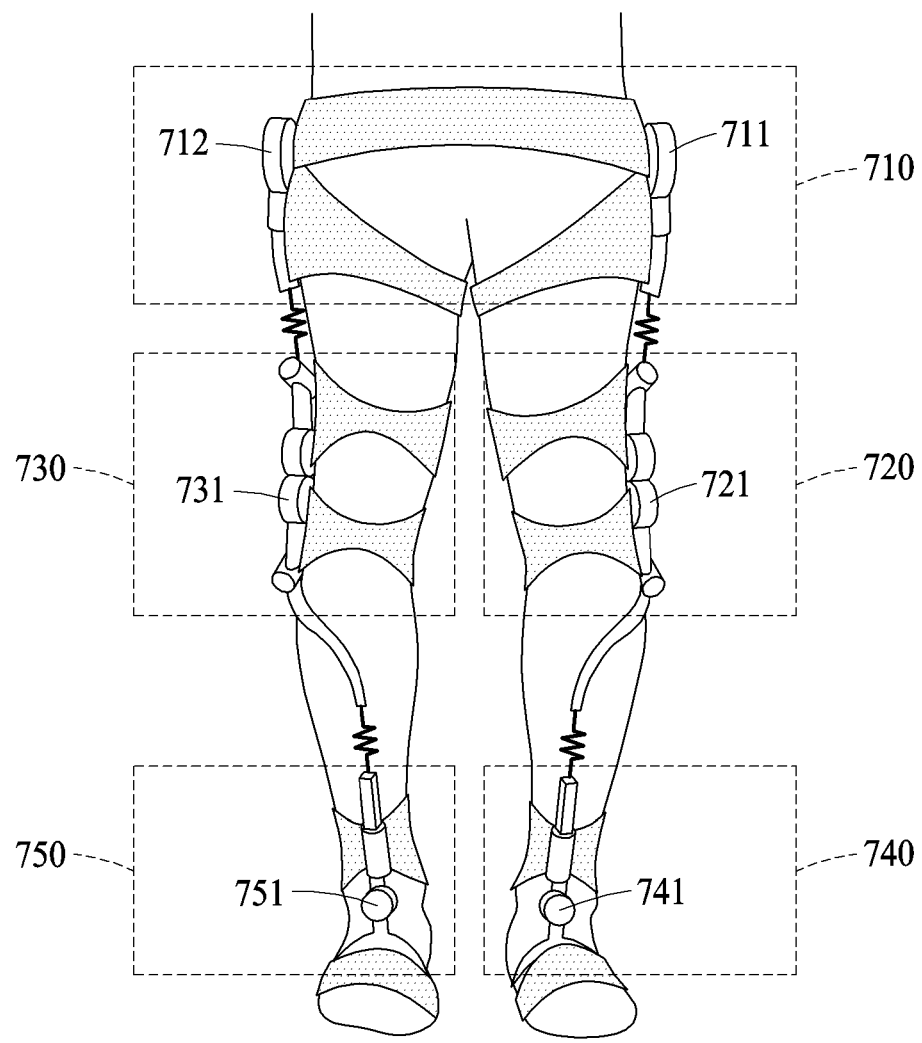
FIG. 7 illustrates a user wearing walking assistance apparatuses including battery managing apparatuses according to at least one example embodiment.

FIG. 7 illustrates a user wearing walking assistance apparatuses 710, 720, 730, 740 and 750 including battery managing apparatuses according to at least one example embodiment. The walking assistance apparatuses 710, 720, 730, 740, and 750 may be wearable electronic devices to be worn on joints of a user separately.

Referring to FIG. 7, the walking assistance apparatus 710 may be attached to hip joint portions of the user to assist flexion motions and/or extension motions of hip joints or assist the user to maintain a pose of an upper body. The walking assistance apparatuses 720 and 730 may be attached to both knees of the user to assist flexion motions and/or extension motions of knee joints or absorb an impact applied to the knees of the user. The walking assistance apparatuses 740 and 750 may be attached to both ankles of the user to assist plantar-flexion motions and/or dorsi-flexion motions of ankle joints of the user or support a weight of the user. The walking assistance apparatuses 710, 720, 730, 740, and 750 may be physically connected through connecting devices.

The walking assistance apparatuses 710, 720, 730, 740, and 750 may be separately used, or may interoperate. For example, the walking assistance apparatuses 710, 720, 730, 740, and 750 may interoperate to assist motions of the user, for example, a walking motion, a sitting motion, and a standing motion. To assist the motions of the user, the walking assistance apparatuses 710, 720, 730, 740, and 750 may each include a motor to assist a motion of a body part to which each of the walking assistance apparatuses 710, 720, 730, 740, and 750 is attached. The walking assistance apparatuses 710, 720, 730, 740, and 750 may each include a motor controller configured to control the corresponding motor, and a battery configured to supply power to the corresponding motor.

In detail, referring to FIG. 7, the walking assistance apparatus 710 may include motors 711 and 712 configured to assist the motions of the hip joints of the user by adjusting angles of frames supporting a pelvis or the hip joints of the user. The walking assistance apparatus 710 may include a motor controller configured to control motions of the motors 711 and 712. The walking assistance apparatus 710 may include a battery configured to store power to be used to operate the motors 711 and 712 and the motor controller.

The walking assistance apparatuses 720 and 730 may respectively include motors 721 and 731 configured to assist the motions of the knee joints of the user by adjusting angles of frames supporting thighs or shanks near the left and right knees to which the walking assistance apparatuses 720 and 730 are attached. The walking assistance apparatuses 720 and 730 may respectively include motor controllers configured to control motions of the motors 721 and 731. The walking assistance apparatuses 720 and 730 may respectively include batteries configured to store power to be used to operate the motors 721 and 731 and the motor controllers.

The walking assistance apparatuses 740 and 750 may include respectively motors 741 and 751 configured to assist the motions of the ankle joints of the user by adjusting angles of frames supporting soles of feet or shanks near the left and right ankles to which the walking assistance apparatuses 740 and 750 are attached. The walking assistance apparatuses 740 and 750 may respectively include motor controllers configured to control motions of the motors 741 and 751. The walking assistance apparatuses 740 and 750 may respectively include batteries configured to store power to be used to operate the motors 741 and 751 and the motor controllers.

Furthermore, to assist the motions of the user for a longer time, the walking assistance apparatuses 710, 720, 730, 740, and 750 may respectively include battery managing apparatuses configured to distribute power stored in the batteries included in the walking assistance apparatuses 710, 720, 730, 740, and 750 to the walking assistance apparatuses 710, 720, 730, 740, and 750.

In sum, the walking assistance apparatuses 710, 720, 730, 740, and 750 may each be considered one of the electronic devices 110, 120, and the motor controller may be included in the power controller of the electronic devices 110, 120 or may be a discrete controller included in the walking assistance apparatuses 710, 720, 730, 740, and 750.

In a case in which the batteries included in the walking assistance apparatuses 710, 720, 730, 740, and 750 are charged with different amounts of charges, the battery managing apparatuses included in the walking assistance apparatuses 710, 720, 730, 740, and 750 may control connections between the batteries and the walking assistance apparatuses 710, 720, 730, 740, and 750 such that the walking assistance apparatuses 710, 720, 730, 740, and 750 may share the amounts of charges of the batteries.

The battery managing apparatuses may determine a mode to control the connections between the batteries and the walking assistance apparatuses 710, 720, 730, 740, and 750 among a single mode, an individual mode, and a parallel mode by comparing SoCs of the batteries included in the walking assistance apparatuses 710, 720, 730, 740, and 750, for example, residual capacities of the batteries or the amounts of charges stored in the batteries. In a case in which the batteries included in the walking assistance apparatuses 710, 720, 730, 740, and 750 have different SoCs, the battery managing apparatuses may control the connections between the batteries and the walking assistance apparatuses 710, 720, 730, 740, and 750 based on the single mode or the individual mode, thereby equalizing the SoCs of the batteries. In a case in which the SoCs of the batteries included in the walking assistance apparatuses 710, 720, 730, 740, and 750 are equal, the battery managing apparatuses may control the connections between the batteries and the walking assistance apparatuses 710, 720, 730, 740, and 750 based on the parallel mode, thereby uniformly using the power charged in the batteries.

In addition, the battery managing apparatuses may request the user to move the batteries included in the walking assistance apparatuses in view of the motions of the body parts to which the walking assistance apparatuses are attached. Weights of the batteries included in the walking assistance apparatuses 720, 730, 740, and 750 attached to the knees and the ankles of the user may interrupt the motions of the knees and the ankles, or apply a strain on the knees and the ankles. The strain applied to the ankles and the knees by the weights of the batteries included in the walking assistance apparatuses 720, 730, 740, and 750 may increase as the ankles and the knees move actively. To reduce the strain applied to the ankles and the knees by the weights of the batteries, the battery managing apparatuses included in the walking assistance apparatuses 720, 730, 740, and 750 may request the user to move the batteries included in the walking assistance apparatuses 720, 730, 740, and 750 to another walking assistance apparatus, for example, to the walking assistance apparatus 710 attached to the hip joints.

The walking assistance apparatus 710 attached to the hip joints may include an additional battery cradle in which the batteries of the walking assistance apparatuses 720, 730, 740, and 750 attached to the ankles and the knees of the user are placed. While the user is moving a battery included in at least one of the walking assistance apparatuses 720, 730, 740, and 750 to the additional battery cradle of the walking assistance apparatus 710, the battery managing apparatus of the walking assistance apparatus 710 may supply power to the walking assistance apparatus from which the battery is separated, among the walking assistance apparatuses 720, 730, 740, and 750.

For example, while the user is moving the battery of the walking assistance apparatus 740 attached to the ankle to the additional battery cradle of the walking assistance apparatus 710, the battery managing apparatus of the walking assistance apparatus 710 may connect the battery of the walking assistance apparatus 710 to the walking assistance apparatus 740. Thus, although the battery of the walking assistance apparatus 740 is separated from the walking assistance apparatus 740, the walking assistance apparatus 740 may continuously receive power from the battery of the walking assistance apparatus 710.

Figure 8:
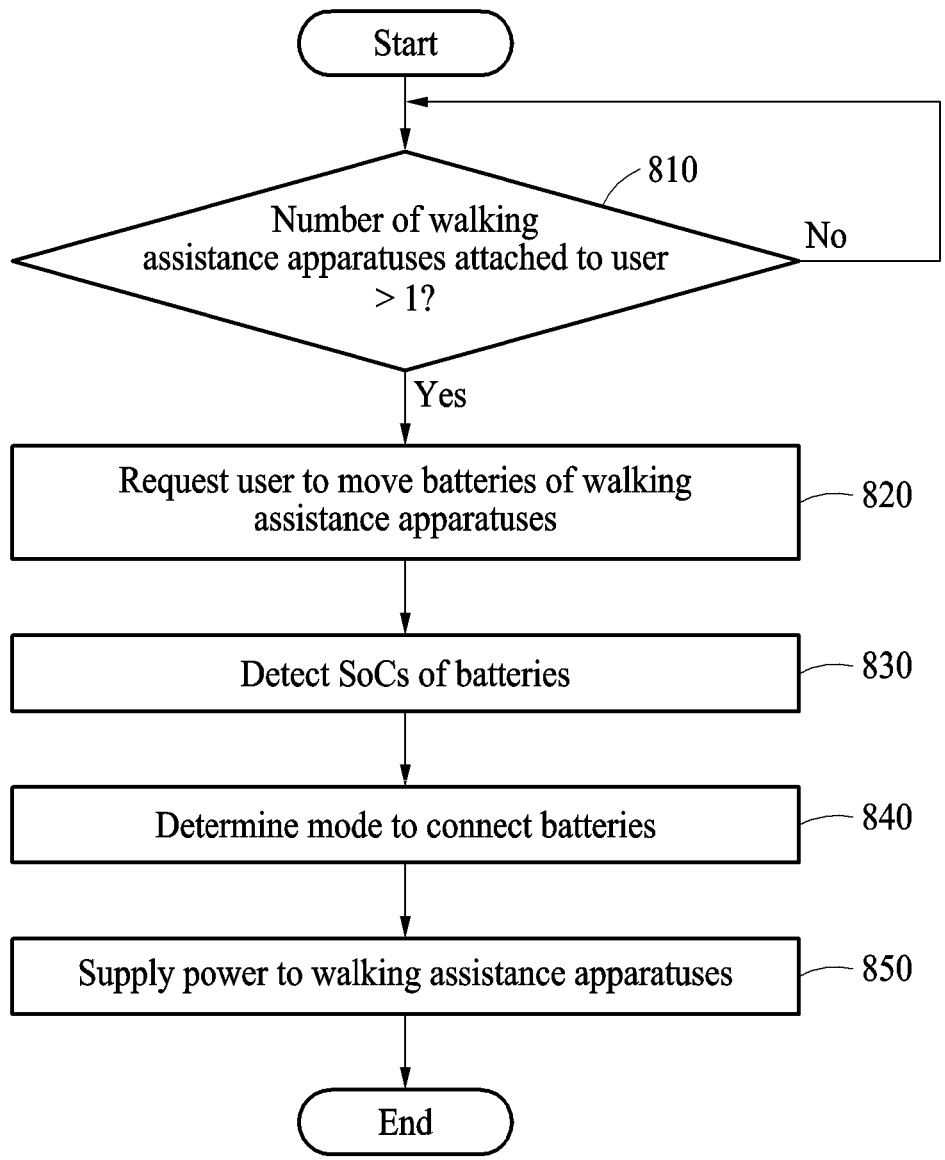
FIG. 8 is flowchart illustrating an operation performed by battery managing apparatuses included in walking assistance apparatuses to be attached to different body parts of a user according to at least one example embodiment.

FIG. 8 is flowchart illustrating an operation performed by battery managing apparatuses included in walking assistance apparatuses to be attached to different body parts of a user according to at least one example embodiment.

Referring to FIG. 8, in operation 810, battery managing apparatuses may verify whether the number of walking assistance apparatuses worn by a user exceeds "1". In a case in which the user connects a plurality of walking assistance apparatuses worn on different body parts, the walking assistance apparatuses may detect each other based on an Ethernet for Control Automation Technology (EtherCAT) or a control area network (CAN).

In a case in which the user wears a plurality of walking assistance apparatuses, the battery managing apparatuses may request the user to move batteries of other walking assistance apparatuses to a walking assistance apparatus including an additional cradle, in operation 820. The operation of the battery managing apparatuses requesting the user to move a battery included in a walking assistance apparatus to another walking assistance apparatus may be performed through a speaker, included in the walking assistance apparatus, outputting an audio signal to the user, through a display, included in the walking assistance apparatus, outputting a text or an image to the user, or through a terminal wirelessly connected to the walking assistance apparatus, for example, a mobile phone, a smart pad, a personal digital assistant (PDA), or a smart watch of the user. While the user is moving the battery of the walking assistance apparatus, the battery managing apparatuses may transmit power of a battery included in the walking assistance apparatus from which the battery is not separated to the walking assistance apparatus from which the battery is separated.

When the battery of the walking assistance apparatus is moved by the user, in operation 830, the battery managing apparatuses may detect SoCs of the batteries. For example, the battery managing apparatuses may detect residual capacities of the batteries which indicate ratios of amounts of charges remaining in the batteries to maximum amounts of charges to be stored in the batteries.

In operation 840, the battery managing apparatuses may determine a mode to connect the batteries to the walking assistance apparatuses based on the detected SoCs of the batteries. The battery managing apparatuses may select the mode from a single mode, an individual mode, and a parallel mode. A result of selecting one of the single mode, the individual mode, and the parallel mode may be provided to the user through an audio signal or a display included in one of the walking assistance apparatuses.

In operation 850, the battery managing apparatuses may supply power of the batteries to the walking assistance apparatuses based on the selected mode.

In a case in which the SoCs of the batteries are equal, the battery managing apparatuses may connect the batteries to the walking assistance apparatuses based on the parallel mode. In detail, the battery managing apparatuses may generate a circuit to supply power to the walking assistance apparatuses by connecting the batteries in parallel. Since the batteries are connected in parallel, the battery managing apparatuses may supply power to the walking assistance apparatuses using the batteries equally.

In a case in which the SoCs of the batteries are not equal, the battery managing apparatuses may connect the batteries to the walking assistance apparatuses based on the single mode or the individual mode. The battery managing apparatuses may identify a battery charged with a greatest amount of charge among the batteries. The battery managing apparatuses may compare a sum of currents that the walking assistance apparatuses are presently consuming to a maximum discharge current of the identified battery.

In a case in which the sum of the currents is less than the maximum discharge current, the battery managing apparatuses may connect the identified battery to the walking assistance apparatuses based on the single mode. In this example, remaining batteries except for the identified battery may be disconnected from the walking assistance apparatuses. Thus, the charge stored in the battery charged with the greatest amount of charge may be output first. In a case in which the sum of the currents is greater than or equal to the maximum discharge current, the battery managing apparatuses may connect the batteries to the corresponding walking assistance apparatuses based on the individual mode. Thus, a malfunction caused when the battery charged with the greatest amount of charge outputs a current greater than or equal to the maximum discharge current may be prevented.

As discussed above, each of the electronic devices may include a discrete battery used to power the driver associated with the electronic device. In some example embodiments, the system including the plurality of electronic devices may reduce power consumption, thus extending the life of the batteries, by setting various ones of the electronic devices to sleep mode based on data from sensors included in the electronic devices. For example, when the data from sensors indicates a user of the electronic devices is at rest (e.g., sitting or lying down), one or more of the electronic devices may enter the sleep mode.

Further, in some example embodiments, the electronic devices may operate cooperatively such that when one of the electronic devices indicates that its associated power supply is low, other ones of the electronic devices may compensate for the low resourced electronic device. For example, if the electronic device associated with a knee of the user is low in resources, the electronic device associated with the hip joint of the user may overextend a hip joint of a user to reduce a range of motion needed by the driver of the knee joint of the user.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of managing batteries included in electronic devices, the method comprising:
   obtaining information related to the batteries;
   comparing residual capacities of the batteries based on the information;
   determining whether a power reception mode for the electronic devices receiving an operating power is a parallel mode, a single mode or an individual mode based on the residual capacities; and
   operating the electronic devices based on the power reception mode such that,
   the electronic devices are set to receive the operating power from a circuit generated by connecting the batteries in parallel, in response to the power reception mode being the parallel mode,
   the electronic devices are set to receive the operating power from a strongest battery having a greatest residual capacity among the batteries, in response to the power reception mode being the single mode, and
   each of the electronic devices is set to receive the operating power from a respective one of the batteries included in each of the electronic devices, in response to the power reception mode being the individual mode.

2. The method of claim 1, wherein the information related to the batteries includes one or more of amounts of charges remaining in the batteries, maximum amounts of currents outputable from the batteries, and current consumptions of the electronic devices.

3. The method of claim 1, wherein the comparing the residual capacities comprises:
   comparing a maximum value of differences between the residual capacities to a threshold.

4. The method of claim 3, wherein the determining the power reception mode comprises:
   determining the power reception mode as the parallel mode, if the maximum value is less than or equal to the threshold.

5. The method of claim 3, wherein the comparing the residual capacities comprises:
   comparing a sum of current consumptions of the electronic devices to a maximum amount of current outputable from the strongest battery among the batteries, if the maximum value exceeds the threshold.

6. The method of claim 5, wherein the determining the power reception mode comprises:
   determining the power reception mode as the single mode, if the sum of the current consumptions is less than the maximum amount of current outputable from the strongest battery.

7. The method of claim 5, wherein the determining the power reception mode comprises:

determining the power reception mode as the individual mode, if the sum of the current consumptions is greater than or equal to the maximum amount of current outputable from the strongest battery.

8. A battery managing apparatus included in an electronic device, the battery managing apparatus comprising:
   a switch connected to a local battery included in the electronic device; and
   a power controller configured to,
      obtain information related to the local battery included in the electronic device and one or more external batteries included in one or more other electronic devices,
      compare residual capacities of the local battery included in the electronic device and the one or more external batteries included in the one or more other electronic devices based on the information,
      determine whether a power reception mode of the electronic device receiving operating power is a parallel mode, a single mode or an individual mode based on the residual capacities, and
      operate the electronic device based on the power reception mode such that,
         the electronic device is set to receive an operating power from a circuit generated by connecting the local battery and the one or more external batteries in parallel, in response to the power reception mode being the parallel mode,
         the electronic device is set to receive the operating power from a strongest battery among the local battery and the one or more external batteries having a greatest residual capacity, in response to the power reception mode being the single mode, and
         the electronic device is set to receive the operating power from the local battery, in response to the power reception mode being the individual mode.

9. The battery managing apparatus of claim 8, wherein the power controller is configured to compare a maximum value of differences between the residual capacities of the local battery and the one or more external batteries to a threshold.

10. The battery managing apparatus of claim 9, wherein the power controller is configured to determine the power reception mode as the parallel mode, if the maximum value is less than or equal to the threshold.

11. The battery managing apparatus of claim 9, wherein the power controller is configured to compare a sum of current consumptions of the electronic device and the one or more other electronic devices to a maximum amount of current outputable from the strongest battery, if the maximum value exceeds the threshold.

12. The battery managing apparatus of claim 11, wherein the power controller is configured to determine the power reception mode as the single mode, when the sum of the current consumptions is less than the maximum amount of current outputable from the strongest battery.

13. The battery managing apparatus of claim 11, wherein the power controller is configured to determine the power reception mode to be the individual mode, if the sum of the current consumptions is greater than or equal to the maximum amount of current outputable from the strongest battery.

14. A battery managing method, comprising:
   measuring residual capacities of batteries respectively included in electronic devices;
   analyzing differences between the residual capacities of the batteries;
   determining whether a power reception mode for the electronic devices receiving an operating power is a parallel mode, a single mode or an individual mode based on the residual capacities; and
   operating the electronic devices based on the power reception mode such that,
      the electronic devices are set to receive the operating power from a circuit generated by connecting the batteries in parallel, in response to the power reception mode being the parallel mode,
      the electronic devices are set to receive the operating power from a strongest battery having a greatest residual capacity among the batteries, in response to the power reception mode being the single mode, and
      each of the electronic devices is set to receive the operating power from a respective one of the batteries included in each of the electronic devices, in response to the power reception mode being the individual mode.

15. The battery managing method of claim 14, wherein the analyzing comprises:
   determining that the residual capacities are similar to each other when a maximum value of the differences between the residual capacities is less than a threshold.

16. The battery managing method of claim 14, wherein the determining of the power reception mode comprises:
   determining the power reception mode as the parallel mode, if a maximum value of the differences between the residual capacities is less than or equal to a threshold.

17. The battery managing method of claim 14, wherein the determining of the power reception mode comprises:
   determining the power reception mode as the individual mode, if a maximum value of the differences between the residual capacities exceeds a threshold and a sum of current consumptions of the electronic devices is greater than or equal to a maximum amount of current outputable from the strongest battery, among the batteries.

18. The battery managing method of claim 14, wherein the determining of the power reception mode comprises:
   determining the power reception mode as the single mode, if a maximum value of the differences between the residual capacities exceeds a threshold and a sum of current consumptions of the electronic devices is less than a maximum amount of current outputable from the strongest battery among the batteries.

19. The battery managing method of claim 18, wherein the determining of the power reception mode as the single mode comprises:
   selecting the strongest battery to provide the operating power for all the electronic devices.

* * * * *